(12) United States Patent
Fischer

(10) Patent No.: US 10,388,610 B2
(45) Date of Patent: Aug. 20, 2019

(54) ELECTRONIC CHIP INSPECTION BY BACKSIDE ILLUMINATION

(71) Applicant: Infineon Technologies AG, Neubiberg (DE)

(72) Inventor: Thomas Fischer, Regensburg (DE)

(73) Assignee: Infineon Technologies AG, Neubiberg (DE)

( * ) Notice: Subject to any disclaimer, the term of this patent is extended or adjusted under 35 U.S.C. 154(b) by 0 days.

(21) Appl. No.: 15/417,618

(22) Filed: Jan. 27, 2017

(65) Prior Publication Data

US 2017/0213796 A1  Jul. 27, 2017

(30) Foreign Application Priority Data

Jan. 27, 2016  (DE) .................. 10 2016 101 452

(51) Int. Cl.
  *G01N 21/64*  (2006.01)
  *H01L 23/544*  (2006.01)
  *G01N 21/95*  (2006.01)
  *G01N 21/956* (2006.01)
  *H01L 21/66*  (2006.01)
  *H01L 21/683* (2006.01)

(52) U.S. Cl.
  CPC .......... *H01L 23/544* (2013.01); *G01N 21/64* (2013.01); *G01N 21/9501* (2013.01); *G01N 21/956* (2013.01); *H01L 21/6836* (2013.01); *H01L 22/12* (2013.01); *H01L 22/34* (2013.01); *G01N 2201/062* (2013.01); *H01L 2223/5448* (2013.01); *H01L 2223/54426* (2013.01); *H01L 2223/54433* (2013.01)

(58) Field of Classification Search
  CPC ....... H01L 23/544; H01L 22/34; G01N 21/64; G01N 21/9501; G01N 21/956
  See application file for complete search history.

(56) References Cited

U.S. PATENT DOCUMENTS

| 4,744,550 A * | 5/1988 | Oglesbee | B28D 5/0052 225/2 |
| 7,629,993 B2 * | 12/2009 | Harless | G01N 21/9501 348/126 |
| 8,224,062 B2 * | 7/2012 | Ohkura | G01N 21/9501 382/149 |
| 8,238,645 B2 * | 8/2012 | Postolov | G01N 21/9501 382/141 |
| 9,025,020 B2 * | 5/2015 | Deslandes | G01N 25/72 348/92 |
| 2005/0008218 A1 * | 1/2005 | O'Dell | G01N 21/9501 382/145 |

(Continued)

FOREIGN PATENT DOCUMENTS

| DE | 102004015326 A1 | 10/2005 |
| DE | 102007006525 A1 | 8/2008 |
| DE | 202015103521 U1 | 8/2015 |

*Primary Examiner* — Christine S. Kim

(57) ABSTRACT

An apparatus for inspecting a plurality of electronic chips singularized from a wafer, wherein the apparatus comprises an electromagnetic radiation source arranged and configured for illuminating at least part of a first main surface of the singularized wafer with electromagnetic radiation, and a detection unit configured for detecting electromagnetic radiation from a side facing a second main surface of the singularized wafer and opposing the first main surface.

18 Claims, 3 Drawing Sheets

(56) References Cited

U.S. PATENT DOCUMENTS

2007/0222974 A1\* 9/2007 Zhao ................. G01N 21/8901
                                                              356/237.1
2015/0204800 A1   7/2015 Mun et al.

\* cited by examiner

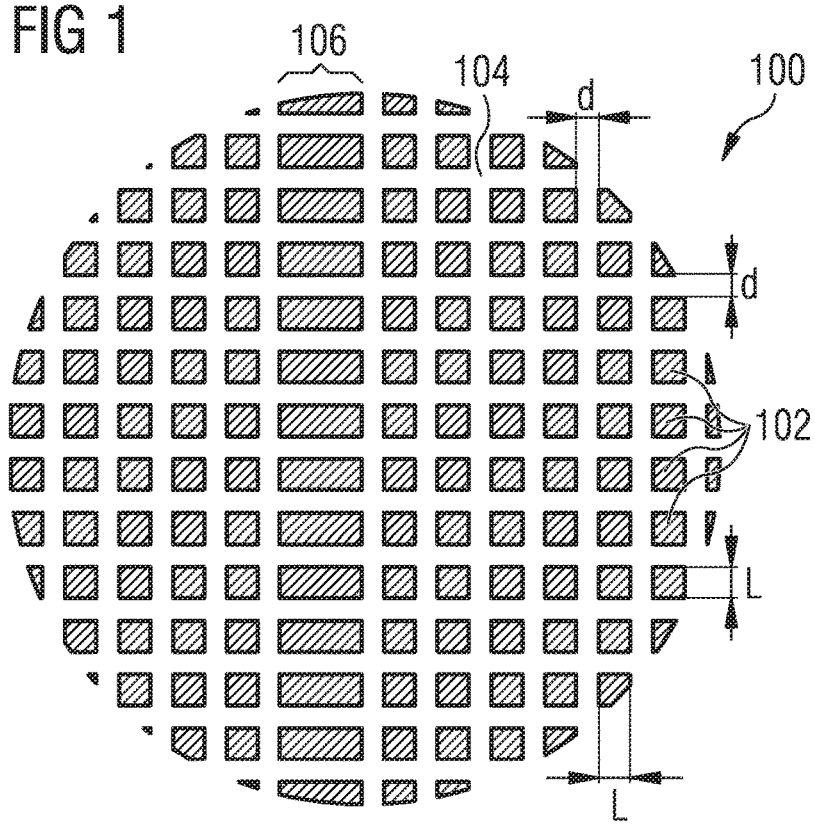
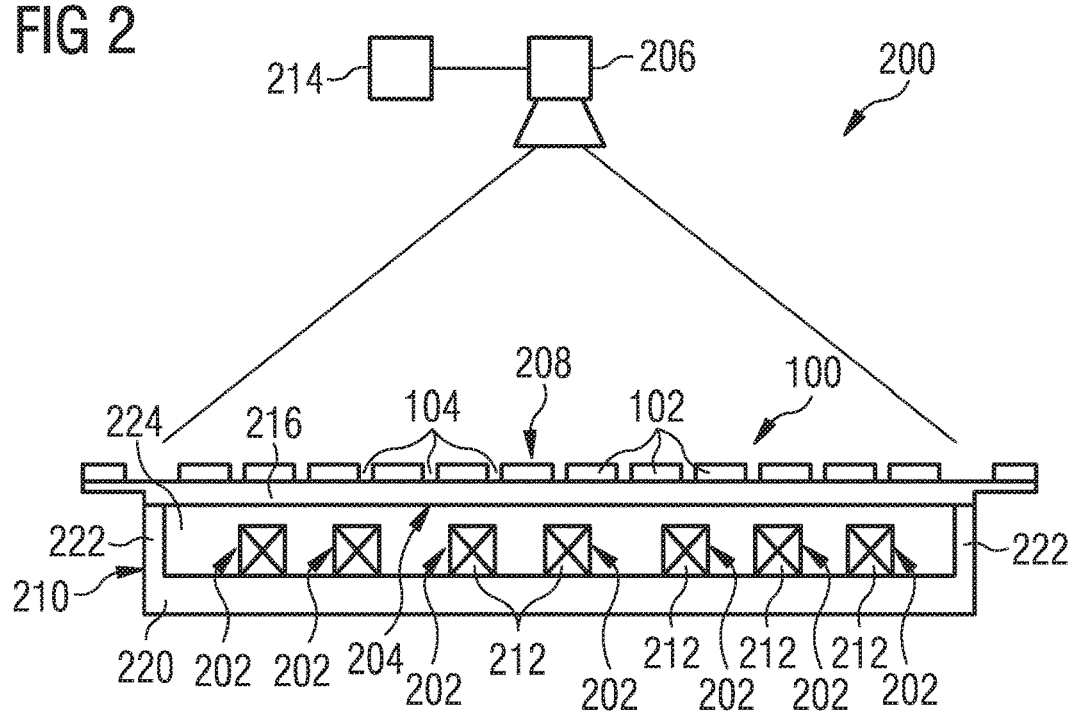

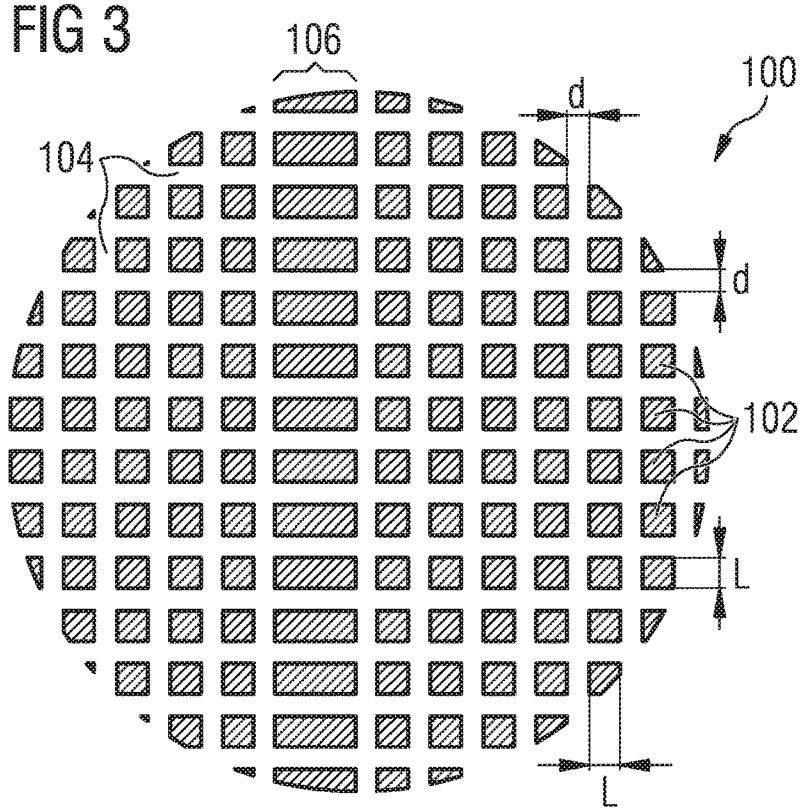
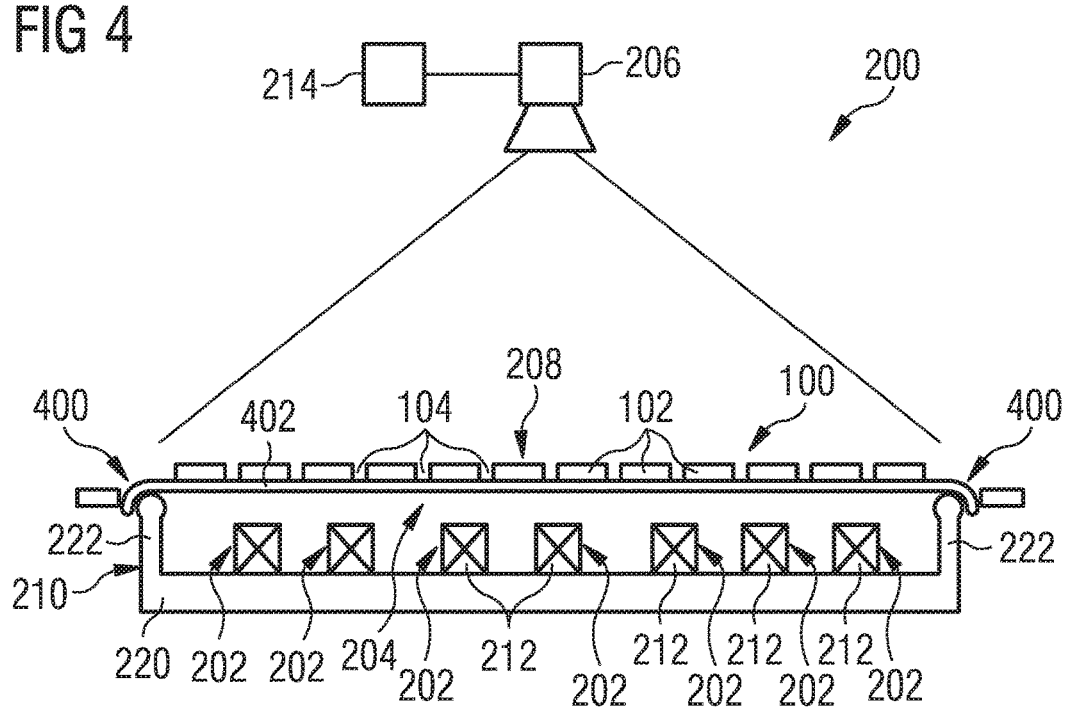

ELECTRONIC CHIP INSPECTION BY BACKSIDE ILLUMINATION

BACKGROUND OF THE INVENTION

Field of the Invention

The present invention relates to an apparatus for and a method of inspecting a plurality of electronic chips singularized from a wafer.

Description of the Related Art

Packages may be denoted as encapsulated electronic chips with electrical connects extending out of the encapsulant and being mounted to an electronic periphery, for instance on a printed circuit board. Before packaging, a semiconductor wafer is singularized into a plurality of electronic chips. One or more of the electronic chips is then encapsulated in an encapsulant of the package. In order to ensure reliability of this process involving also a pick and place procedure, it may be advantageous to inspect the wafer or the electronic chips.

SUMMARY OF THE INVENTION

There may be a need to provide a possibility of reliably inspecting a wafer singularized into a plurality of electronic chips.

According to an exemplary embodiment, an apparatus for inspecting a plurality of electronic chips singularized from a wafer is provided, wherein the apparatus comprises an electromagnetic radiation source arranged and configured for illuminating at least part of a first main surface of the singularized wafer with electromagnetic radiation, and a detection unit configured for detecting electromagnetic radiation from a side facing a second main surface of the singularized wafer and opposing the first main surface.

According to another exemplary embodiment, a method of inspecting a plurality of electronic chips singularized from a wafer is provided, wherein the method comprises illuminating at least part of a first main surface of the singularized wafer with electromagnetic radiation, and detecting electromagnetic radiation from a side facing a second main surface of the singularized wafer and opposing the first main surface.

According to an exemplary embodiment of the invention, already singularized electronic chips being consequently already spaced with regard to one another but which may still be arranged in accordance with a previous wafer geometry may be inspected by a backside illumination and front side detection of electromagnetic radiation. Detecting backside illumination on a front side allows to obtain a pronounced dark-light pattern in a detection image, whereas dark regions may correspond to positions of the electronic chips and light regions may correspond to gaps between the electronic chips. In a backside illumination arrangement, it has turned out that structures on either of the surfaces of the electronic chips are not disturbing for the inspection. By taking this measure, reliable information indicative of positioning, orientation, mutual spatial relation, etc. between the electronic chips may be obtained in a simple and failure robust way. Consequently, a procedure of singularizing the chips from the wafer, picking them up from a carrier such as a carrier foil, placing them on a chip carrier such as a lead frame, and packaging them for instance by an encapsulation can be rendered highly accurate. Errors (such as inappropriate singularization, for instance caused by a broken saw blade) which may occur during such a procedure may be detected early and may be compensated, if desired.

DESCRIPTION OF FURTHER EXEMPLARY EMBODIMENTS

In the following, further exemplary embodiments of the apparatus and the method will be explained.

In the context of the present application, the term "wafer" may particularly denote a semiconductor substrate which has been processed to form a plurality of integrated circuit elements in an active region of the wafer and which is, when being inspected according to an exemplary embodiment, already singularized into a plurality of separate electronic chips. For example, a wafer may have a disk shape and may comprise a matrix-like arrangement of electronic chips in rows and columns. It is possible that a wafer has a circular geometry or a polygonal geometry (such as a rectangular geometry or a triangular geometry).

In the context of the present application, the term "electronic chip" may particularly denote a naked die, i.e. a non-packaged (for instance non-molded) chip made of a processed semiconductor, for instance a singulated piece of a semiconductor wafer. A semiconductor chip may however also be an already packaged (for instance molded or laminated) die. One or more integrated circuit elements (such as a diode, a transistor, etc.) may be formed within the semiconductor chip. Such a semiconductor chip may be equipped with a metallization, in particular with one or more pads.

In the context of the present application, the term "singularizing" may particularly denote the procedure of separating an integral wafer into a plurality of separate electronic chips as sections of the previous wafer. Such a singularization may be accomplished by sawing, laser cutting, etching, etc. It is also possible to accomplish singularization by self-dicing (for instance by selectively thinning regions of the wafer between adjacent electronic chips, followed by a singularization by tearing or expanding the wafer to thereby break it into separated electronic chips at the thinned regions, serving as predetermined breaking points.

In the context of the present application, the term "electromagnetic radiation" may particularly denote photons of any desired wavelength or wavelength range. For example, the electromagnetic radiation may be visible light (in particular having a wavelength in a range between 400 nm and 800 nm), ultraviolet light, infrared light, X-rays, etc. Wavelength and intensity of the electromagnetic radiation can be selected so as to obtain a proper dark-light pattern in a detected image.

In an embodiment, the apparatus comprises a receptacle (such as a chuck) configured so that the singularized wafer is mountable on or over the receptacle. Such a receptacle may have a protruding annular support section on which the disk-shaped wafer—which may be, in turn, located on a carrier—may be supported along a circumference thereof. The elevated annular support section may be connected to a plate-shaped base of the receptacle. By such an arrangement, both handling and inspection of the already singularized mutually spaced electronic chips on the carrier is possible.

In an embodiment, the electromagnetic radiation source is arranged on and/or in the receptacle. A volume delimited between the above described annular support and base of a substantially cup-shaped chuck may be efficiently used for accommodating the electromagnetic radiation source for backside illumination of the wafer. Consequently, a compact arrangement may be obtained.

In an embodiment, the electromagnetic radiation source comprises at least one of the group consisting of a two-dimensional array of electromagnetic radiation elements, and an electromagnetic radiation emitting layer. With a two-dimensional array of electromagnetic radiation elements (such as an LED carpet), a substantially homogeneously illuminated area section may be defined which may have substantially the same area as the wafer. Such a two-dimensional array may be properly placed in an accommodation volume of the above described receptacle. An electromagnetic radiation emitting layer may be advantageously configured to form part of the carrier carrying the singularized electronic chips of the wafer on the receptacle. Such an embodiment allows for a specifically compact configuration.

In an embodiment, the electromagnetic radiation source comprises at least one light-emitting diode (LED). Light emitting diodes are lightweight, compact, energy-efficient light sources which can be flexibly arranged to form a two-dimensional irradiation area homogeneously illuminating substantially the entire backside of the wafer. Alternatively, other light sources can be implemented such as a white light lamp, a mercury vapor lamp, a laser, an arc lamp, a flash tube, a fluorescence lamp, etc.

In an embodiment, the electromagnetic radiation source may be spatially fixed, in particular fully illuminating the entire back surface of the singularized wafer with small effort.

In another embodiment, the electromagnetic radiation source may be spatially movable, in particular illuminating only a variable subsection of the entire back surface of the singularized wafer so as to allow to specifically inspect only portions of the wafer (for instance a portion which has been identified beforehand as potentially critical).

In yet another embodiment, the electromagnetic radiation source may comprise different electromagnetic radiation elements operating at different wavelengths or wavelength ranges. In still another embodiment, the electromagnetic radiation source may have an adjustable wavelength or wavelength range of emitted electromagnetic radiation. For example, the electromagnetic radiation source may be configured for emitting a first wavelength or first wavelength range (for instance in the optical range) during inspection. Additionally, the electromagnetic radiation source may be configured for emitting a second wavelength or second wavelength range (for instance in the ultraviolet range) for converting a carrier (in particular a carrier foil) supporting the singularized wafer from a previously adhesive state into a less adhesive or non-adhesive state. This simplifies subsequent detachment (for example by picking) of individual electronic chips from the carrier for further processing (for instance in terms of packaging). Such UV activatable carrier foils may be synergistically controlled by the same electromagnetic radiation source which also contributes to the inspection.

In an embodiment, the detection unit is configured for detecting electromagnetic radiation along at least part of a circumferential edge of the singularized wafer. This allows to obtain information with regard to the exterior limits of the singularized wafer. Such an information may be helpful in particular for alignment and positioning purposes.

In an embodiment, the detection unit is configured for detecting electromagnetic radiation passing through gaps between respectively adjacent singularized electronic chips of the singularized wafer. Dark portions of the light pattern may be identified as singularized electronic chips or other sections of the wafer, whereas light portions of the light pattern may be identified as gaps in between. This allows to identify potential issues with the singularization procedure, for instance erroneously still connected electronic chips.

In an embodiment, the apparatus comprises a determining unit (for instance a processor, such as a microprocessor or a central processing unit, CPU) configured for determining information relating to at least one of the singularized wafer and the electronic chips based on the detected electromagnetic radiation. In order to determine such information, the determining unit may carry out image processing tasks such as pattern recognition (for instance for identifying individual electronic chips with a certain expected shape and dimension, identifying a circumference of the singularized wafer based on an expected circumferential shape of spaced electronic chips, etc.).

In an embodiment, the apparatus comprises an expansion unit configured for spatially expanding a flexible carrier carrying the electronic chips to thereby increase a distance between adjacent electronic chips during inspection. For example, the singularized wafer with the mutually spaced electronic chips may be located on a flexible, in particular elastic, carrier foil, which may be adhesive for preventing undesired detachment of electronic chips. When the expansion unit applies an outwardly directed pulling force on such a flexible carrier foil, the carrier foil with the electronic chips attached thereon will spatially expand. This will result in an increase of the gaps between adjacent electronic chips. When the inspection, based on the backside illumination and front side detection of the electromagnetic radiation passing through the gaps, is carried out in the expanded state of the carrier foil and the singularized wafer, the contrast and therefore the detection accuracy may be increased.

In an embodiment, the apparatus comprises the above described carrier for carrying the electronic chips and being transparent for the electromagnetic radiation. Thus, the material and dimensional configuration of the properties of the carrier can be selected so that the backlight radiation of any suitable wavelength or wavelength range is capable of propagating through the carrier without significant loss of intensity. For instance, the carrier foil may be so thin that it is transparent to a sufficient degree to allow the electromagnetic radiation to pass the carrier foil without pronounced absorption or reflection. Preferably, the material of the carrier (for instance a carrier plate) is selected so that it is transparent for the used electromagnetic radiation, for instance light. This improves the contrast of the detected image and thus the precision of the inspection.

In an embodiment, the electromagnetic radiation source is integrated in or is attached to the carrier. For example, organic light emitting diodes (OLEDs) may be implemented into such an illuminating carrier, for instance configured as a foil or a plate. This allows for a compact configuration of the apparatus. More specifically, such an illuminating foil may be a fluorescent tape (for instance emitting electromagnetic radiation upon application of an electric current). More generally, a carrier (in particular a carrier foil) may be configured as light emitting element or electromagnetic radiation source.

In an embodiment, the apparatus comprises fluorescent ink configured for marking at least part of the electronic chip with an alignment marker of fluorescent ink. In particular, ink marking of electronic chips is possible for such electronic chips which have been identified as waste or reject. By fluorescent ink marking of such electronic chips, corresponding electronic chip may be identified with the inspection apparatus.

In an embodiment, the method comprises detecting electromagnetic radiation having passed from the first main surface through the singularized wafer to the second main surface. In the apparatus, the detection unit may be configured correspondingly. By such an architecture of arranging electromagnetic radiation source and detection unit to face opposing main surfaces of the singularized wafer, only electromagnetic radiation passing through the singularized wafer may be detected, ensuring high contrast and consequently high resolution.

In an embodiment, the method comprises determining information relating to the singularized wafer and/or the electronic chips based on the detected electromagnetic radiation. In particular, information with regard to the mutual arrangement of the individual electronic chips with regard to one another may be derived.

In an embodiment, the determined information comprises a distance between adjacent electronic chips in at least one direction. In particular, the dimension of a gap between neighboured electronic chips may be determined along one or two (in particular perpendicular) directions.

In an embodiment, the determined information comprises a dimension of at least part of the electronic chips in at least one direction. In particular, the dimension of an electronic chip may be determined along one or two (in particular perpendicular) directions.

In an embodiment, the determined information comprises the existence of at least one missing singularization region in which adjacent electronic chips have not been singularized. For instance in case of failure of a saw blade, it may happen that two neighboured rows of electronic chips remain unintentionally connected to one another rather than being separated from one another. In such an event, the dimension of the electronic chips can be found as substantially twice of an expected dimension. This allows the apparatus to trigger an event, for instance an alarm, post processing of the improperly singularized wafer, classification of the corresponding wafer section as defective or waste, etc.

In an embodiment, the determined information comprises a number and/or a position of one or more alignment markers on at least part of the electronic chips. For instance, the positioning of one or more corresponding reference dies (for example electronic chip with a mirror surface, etc.) of the singularized wafer may be detected.

In an embodiment, the determined information comprises a position of at least one of the electronic chips. This increases the accuracy of a subsequent picking procedure, for instance for encapsulating individual electronic chips for the formation of readily finished packages.

In an embodiment, the determined information comprises a characterization of an exterior edge of at least part of the singularized wafer. This information can be used for alignment purposes.

In an embodiment, it is also possible to implement further electrical circuitry. It is possible to use a sliding contact, a plug contact, a cable guided circuitry, a printed circuit board, etc.

In an embodiment, the electronic chip is a power semiconductor chip. Such a power semiconductor chip may have integrated therein one or multiple integrated circuit elements such as transistors (for instance field effect transistors like metal oxide semiconductor field effect transistors and/or bipolar transistors such as insulated gate bipolar transistors) and/or diodes. Exemplary applications which can be provided by such integrated circuit elements are switching purposes. For example, such another integrated circuit element of a power semiconductor device may be integrated in a half-bridge or a full bridge. Exemplary applications are automotive applications.

The one or more semiconductor chips may comprise at least one of the group consisting of a diode, and a transistor, more particularly an insulated gate bipolar transistor. For instance, the one or more electronic chips may be used as semiconductor chips for power applications for instance in the automotive field. In an embodiment, at least one semiconductor chip may comprise a logic IC or a semiconductor chip for RF power applications. In one embodiment, the semiconductor chip(s) may be used as one or more sensors or actuators in microelectromechanical systems (MEMS), for example as pressure sensors or acceleration sensors.

As substrate or wafer for the semiconductor chips, a semiconductor substrate, preferably a silicon substrate, may be used. Alternatively, a silicon oxide or another insulator substrate may be provided. It is also possible to implement a germanium substrate or a III-V-semiconductor material. For instance, exemplary embodiments may be implemented in GaN or SiC technology.

The above and other objects, features and advantages of the present invention will become apparent from the following description and the appended claims, taken in conjunction with the accompanying drawings, in which like parts or elements are denoted by like reference numbers.

BRIEF DESCRIPTION OF THE DRAWINGS

The accompanying drawings, which are included to provide a further understanding of exemplary embodiments of the invention and constitute a part of the specification, illustrate exemplary embodiments of the invention.

In the drawings:

FIG. 1 shows a plan view of a singularized wafer already singularized into a plurality of electronic chips and inspected by a method according to an exemplary embodiment of the invention.

FIG. 2 shows a cross-sectional view of an apparatus for inspecting the singularized wafer according to FIG. 1 composed of the plurality of already singularized electronic chips by backside illumination according to an exemplary embodiment of the invention.

FIG. 3 shows a plan view of a singularized wafer already singularized into a plurality of electronic chips and inspected by a method according to an exemplary embodiment of the invention.

FIG. 4 shows a cross-sectional view of an apparatus for inspecting the singularized wafer according to FIG. 3 composed of the plurality of already singularized electronic chips by backside illumination according to another exemplary embodiment of the invention.

DETAILED DESCRIPTION OF EXEMPLARY EMBODIMENTS

Figure 5:
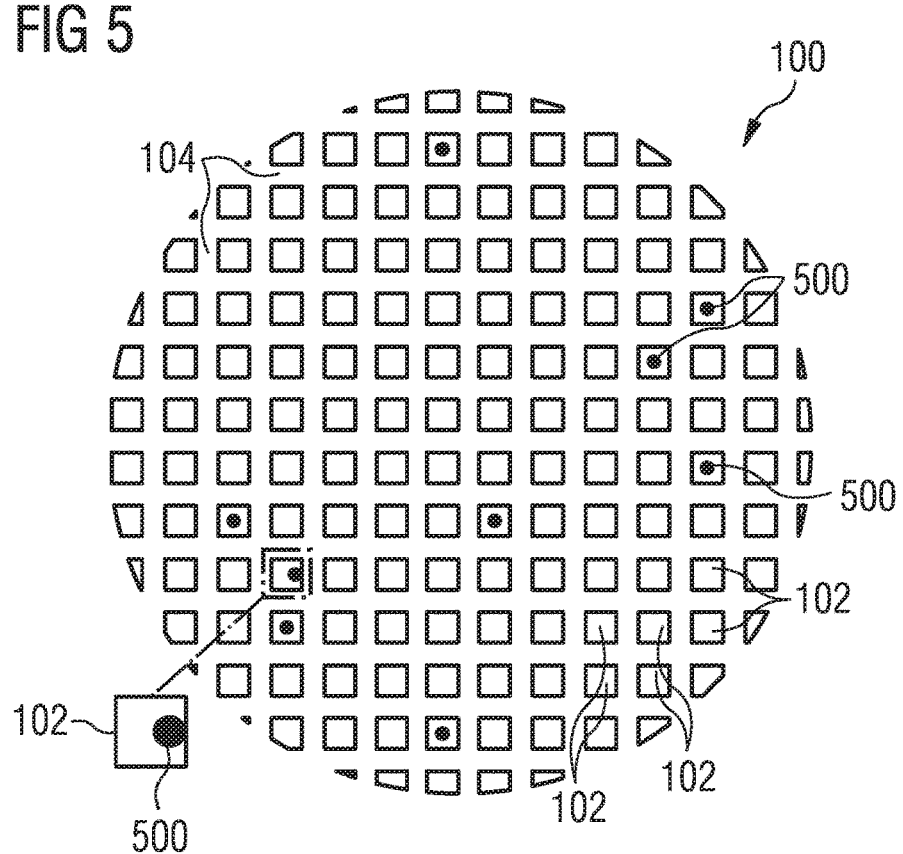
FIG. 5 shows a plan view of a singularized wafer already singularized into a plurality of electronic chips with ink markers and inspected by a method according to an exemplary embodiment of the invention.

The illustration in the drawing is schematically and not to scale.

Before exemplary embodiments will be described in more detail referring to the figures, some general considerations will be summarized based on which exemplary embodiments have been developed.

According to an exemplary embodiment of the invention, background illumination of singularized electronic chips is performed for control purposes after singularization from a wafer.

For separated electronic chips or dies on a carrier (for instance a saw foil) it is presently a challenge to reliably and automatically determine information indicative of edges, etc. Structures and different materials additionally render it difficult to reliably identify such information on the front side or the back side of a singularized wafer.

An exemplary embodiment of the invention overcomes this conventional shortcoming by carrying out background illumination of the singularized wafer for optical control after singularization into electronic chips. This allows to improve chip edge recognition. It is also possible to automatically monitor chip distances and/or chip dimensions after separation. Also a separation rate (i.e. as to whether all electronic chips have been properly singularized) may be automatically controlled. Furthermore, it is possible to quickly determine the position of the electronic chips on a carrier frame or a carrier foil for different subsequent procedures (such as automatic optical inspection, frame controller, etc.). Also determining the position and controlling the number of ink dots of a separated wafer as well as a control of the ink dot position on a chip is possible (such as automatic optical inspection, frame inking).

The adaptation of the illumination architecture according to an exemplary embodiment of the invention, i.e. the implementation of a background illumination (for instance arranged in a receptacle such as a carrier) has turned out to be highly advantageous. Accordingly, the separated wafer can be illuminated from a bottom side so that any influence from the front side may be excluded. More generally, an exemplary embodiment of the invention renders it possible to illuminate a body from a backside and to identify geometrical dimensions using optical image recognition. Detection from the opposing side has turned out to be possible without disturbing influences from surface features of the illuminated body, i.e. separated wafer.

FIG. 1 shows a plan view of a wafer 100, here embodied as an already processed semiconductor wafer with integrated circuit elements therein. In the state of the wafer 100 shown in FIG. 1 it has already been singularized, by sawing, into a plurality of electronic chips 102. By an apparatus 200 shown in FIG. 2, the individual electronic chips 102 of the singularized wafer 100 may be geometrically inspected according to an exemplary embodiment of the invention.

As can be taken from FIG. 1, void spaces or gaps 104 are formed between neighboring electronic chips 102 as a result of the singularization. In the shown embodiment, the gaps 104 have the same vertical and horizontal extension, i.e. d, wherein vertical and horizontal extension may also be different and gaps 104 may have different values for different sections of the singularized wafer 100.

Furthermore, the electronic chips 102 have the same vertical and horizontal dimension, i.e. L, wherein vertical and horizontal dimension may also be different. FIG. 1 also shows a wafer section with an erroneously missing singularization region 106 in which adjacent electronic chips 102 have not been singularized, for instance due to breakage of a sawing blade used for sawing the wafer 100. Although the individual chips 102 have been singularized from the previously integral wafer 100, their arrangement is still in accordance with the previous wafer shape or wafer geometry, since the electronic chips 102 may be located on a common carrier 216, as shown in FIG. 2.

FIG. 2 shows a cross-sectional or side view of an apparatus 200 for inspecting the singularized wafer 100 according to FIG. 1 composed of the plurality of already singularized electronic chips 102 by backside illumination with light according to an exemplary embodiment of the invention.

The apparatus 200 is configured for individually inspecting each or a part of the plurality of electronic chips 102 singularized from the previously integrally formed wafer 100. By this inspection, geometrical information characterizing individual ones or groups of the electronic chips 102 may be derived. The apparatus 200 comprises an electromagnetic radiation source 202, here configured as a two-dimensional array of electromagnetic radiation elements 212. The electromagnetic radiation elements 212 are here embodied as coplanar light emitting diodes arranged equidistantly in accordance with a regular pattern in a plane perpendicular to the paper plane of FIG. 2 to obtain substantially homogeneous illumination of the lower side of the matrix-like arrangement of the electronic chips 102. The electromagnetic radiation source 202 is hence arranged and configured for illuminating substantially an entire first main surface 204 (according to FIG. 2 a lower surface) of the electronic chips 102 of the singularized wafer 100 with electromagnetic radiation, in the shown embodiment with visible light.

A detection unit 206, such as a camera (for example a CMOS camera or a CCD camera), is arranged to face a second main surface 208 (an upper surface according to FIG. 2) of the electronic chips 100 of the singularized wafer 100. The second main surface 208 opposes the first main surface 204. More specifically, the detection unit 206 is configured for detecting electromagnetic radiation passing through the gaps 104 between adjacent singularized electronic chips 102 of the singularized wafer 100. Hence, the detection unit 206 may capture a two-dimensional image of the second main surface 208 of the still wafer-like arranged electronic chips 102.

The functioning principle of the apparatus 200 is therefore a backside illumination of the first main surface 204 by an electromagnetic radiation source 202 arranged to face the first main surface 204, in combination with a front side detection of electromagnetic radiation passing through the array of electronic chips 102 (in particular propagating only through the gaps 104 between the light absorbing electronic chips 102). The latter is accomplished by detection unit 206 arranged to face the second main surface 208. In other words, the monitoring architecture according to an exemplary embodiment of the invention is based on a transmission measurement rather than on a reflection measurement. Hence, the executed inspection method comprises detecting electromagnetic radiation having passed from the first main surface 204 through gaps 104 within the singularized wafer 100 to the second main surface 208. By taking this measure, a high contrast image is obtained which is not disturbed by any structures which may be formed on either of the main surfaces 204, 208 of the electronic chips 102 assigned to the separated wafer 100.

Furthermore, the apparatus 100 comprises a receptacle 210, which may be denoted as chuck, and which is configured so that the singularized wafer 100 is mountable on or over the receptacle 210. In the shown embodiment, the electronic chips 102 are mounted on the receptacle 210 face up, i.e. with their active regions facing detection unit 206 rather than facing the electromagnetic radiation source 202. The term "active region" may denote a surface semiconductor portion of the electronic chips 102 in which one or more integrated circuit elements are formed, such as transistors, diodes, etc., and which may be metallized. A surface metallization may be provided as one or more chip pads on the active region. However, it is also possible that the electronic chips 102 are mounted face down, i.e. with their active region facing the electromagnetic radiation source 202 rather than facing the detection unit 206. The receptacle 210 may or may not be the same process chuck on which the wafer 100 is located during singularization by sawing. The receptacle 210 comprises a plate-shaped bottom wall 220 integrally connected with a vertically protruding annular sidewall 222. According to FIG. 2, the electromagnetic radiation source 202 is arranged within an accommodation volume 224 defined by the receptacle 210.

The apparatus 200 moreover comprises a carrier 216 for carrying the electronic chips 102 and being at least partially transparent for the electromagnetic radiation. In the shown embodiment, the carrier 216 is a transparent glass plate, which may include a vacuum channel (not shown) for holding the wafer 100/the electronic chips 102 thereof by a vacuum suction force. More specifically, the glass plate may be provided on its upper surface with grooves in fluid communication with an interior channel within the glass plate for providing the vacuum suction force from an exterior of the glass plate.

Furthermore, the apparatus 100 comprises a determining unit 214 (which may be configured as a processor) configured for determining information relating to the electronic chips 102 of the singularized wafer 100 based on the detected electromagnetic radiation, i.e. based on the image data transmitted to the determining unit 214 by the detection unit 206. Hence, the determining unit 214 may be supplied with the data relating to the captured image(s) from the detection unit 206. The determining unit 214 may carry out image processing tasks such as pattern recognition to determine features geometrically characterizing the arrangement of the electronic chips 102 as a whole and/or in relation to one another. The determining unit 214, evaluating detection data from the detection unit 206, is therefore capable of determining information relating to the singularized wafer 100 and/or the electronic chips 102 based on the detected electromagnetic radiation. This determined information may comprise the value of the distance d between adjacent electronic chips 102 in one or two orthogonal directions. Additionally or alternatively, the determined information may comprise the dimension L of the electronic chips 102 in one or two orthogonal directions. Furthermore, the determined information may comprise an identification of the existence or even the location of the above described missing singularization region 106 in which adjacent electronic chips 102 have not been singularized due to a failure in the singularization procedure. It is also possible that the determined information comprises an absolute or a relative (i.e. referring to a reference) position of a respective one of the electronic chips 102.

The embodiment shown in FIG. 1 and FIG. 2 relates to an automatic control of the separation rate. The receptacle 210 or chuck is implemented in accordance with a background illumination architecture by LEDs as electromagnetic radiation source 202. This architecture makes it possible to exclude influences of the inspected separated wafer 100 surface on the determination of the mentioned information. Thus, it becomes possible with high accuracy to automatically determine and map non-separated electronic chips 102, to automatically determine and map only partially separated electronic chips 102 (see missing singularization region 106), to rapidly and precisely determine the position of individual electronic chips 102 (pre-alignment) on the receptacle 210, and to render a cumbersome fully manual inspection by an operator dispensable. The apparatus 200 according to FIG. 2 may be used for automated optical inspection.

FIG. 3 shows a plan view of a singularized wafer 100 already singularized into a plurality of electronic chips 102 and inspected by a method according to an exemplary embodiment of the invention.

FIG. 4 shows a cross-sectional view of an apparatus 200 for inspecting the singularized wafer 100 according to FIG. 3 composed of the plurality of already singularized electronic chips 102 by backside illumination according to another exemplary embodiment of the invention.

A difference between the apparatus 200 shown in FIG. 4 compared to the apparatus 200 shown in FIG. 2 is that, according to FIG. 4, the carrier 216 is not implemented as an optically transparent rigid plate but in contrast to this by a flexible adhesive and optically transparent carrier foil as flexible carrier 402. For example, the flexible carrier 402 may be configured as a light-transparent foil having a thickness in a range between 90 µm and 120 µm, for instance made of polyvinylchloride or polyolefin. This carrier foil functionally cooperates with an expansion unit 400 located on or forming part of the receptacle 210 and configured for spatially expanding (in a horizontal plane in which the electronic chips 102 are arranged) the flexible carrier 402 carrying the electronic chips 102. Thereby, it is possible to temporarily increase, during inspection, the distance d between adjacent electronic chips 102. This increases the accuracy of the derived information. Hence, according to FIG. 4, a chuck with expansion function is provided.

The apparatus 200 according to FIG. 4 may be used for process control after singularization. In particular, a detection of a misalignment of a sawing track may be carried out with the apparatus 200 according to FIG. 4.

FIG. 5 shows a plan view of a wafer 100 already singularized into a plurality of electronic chips 102, some of which being provided with ink alignment markers 500, and inspected by a method according to an exemplary embodiment of the invention. As can be taken from FIG. 5, several of the electronic chips 102 have been marked with a corresponding dot of fluorescent ink as a respective fluorescent alignment marker 500 of the respective electronic chip 102. For instance, electronic chips 102 identified as defective or waste can be marked with such an alignment marker 500.

Figure 6:
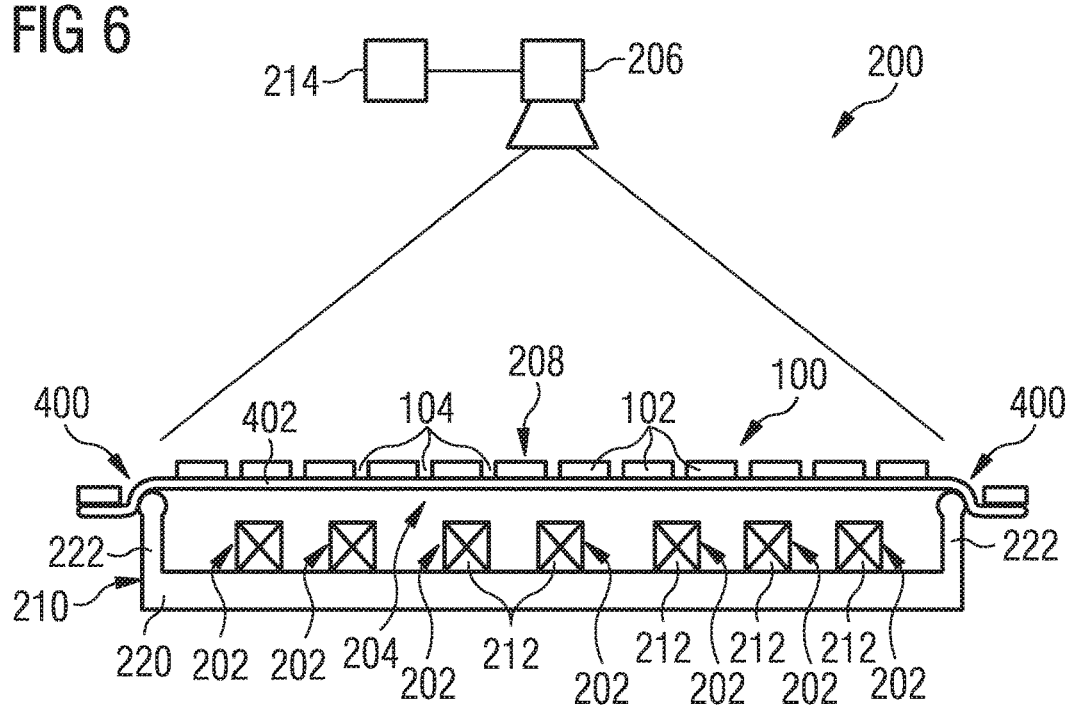
FIG. 6 shows a cross-sectional view of an apparatus for inspecting the singularized wafer according to FIG. 5 composed of the plurality of already singularized electronic chips by backside illumination according to still another exemplary embodiment of the invention.

FIG. 6 shows a cross-sectional view of an apparatus 200 for inspecting the singularized wafer 100 according to FIG. 5 composed of the plurality of already singularized electronic chips 102 by backside illumination according to still another exemplary embodiment of the invention.

The embodiment according to FIG. 6 corresponds to the embodiment according to FIG. 4. However, according to FIG. 6, the determining unit 214 is additionally configured for determining a number and/or a respective position of the alignment markers 500 on some of the electronic chips 102. This can be done by pattern recognition. The apparatus 200 according to FIG. 6 may inspect as to whether the correct electronic chips 102 are inked, and as to whether an ink position is correct, etc. In addition to the information which can be determined according to the embodiment of FIG. 3 and FIG. 4, it is possible with the embodiment according to FIG. 5 and FIG. 6 to quickly carry out a position control of electronic chips 102 with ink alignment marker 500 and to compare the position with an electronic map, to carry out a number control of electronic chips 102 with ink alignment marker 500 and compare the number with an electronic map, and/or to rapidly determine the position of the ink alignment marker 500 and an electronic chip 102.

In any of the described embodiments, it is possible to, additionally or alternatively, carry out edge recognition of the wafer 100 and/or or the electronic chips 102 thereof, for example for alignment purposes.

It should be noted that the term "comprising" does not exclude other elements or features and the "a" or "an" does not exclude a plurality. Also elements described in association with different embodiments may be combined. It should also be noted that reference signs shall not be construed as limiting the scope of the claims. Moreover, the scope of the present application is not intended to be limited to the particular embodiments of the process, machine, manufacture, composition of matter, means, methods and steps described in the specification. Accordingly, the appended claims are intended to include within their scope such processes, machines, manufacture, compositions of matter, means, methods, or steps.

What is claimed is:

1. An apparatus for inspecting a plurality of electronic chips singularized from a wafer, the apparatus comprising:
    an electromagnetic radiation source arranged and configured for illuminating at least part of a first main surface of the singularized wafer with electromagnetic radiation;
    a detection unit configured for detecting electromagnetic radiation from a side facing a second main surface of the singularized wafer and opposing the first main surface, wherein the detection unit is configured for detecting electromagnetic radiation along at least part of a circumferential edge of the singularized wafer;
    a receptacle configured so that the wafer is mountable on or over the receptacle and configured for both handling and inspection of the plurality of electronic chips; and
    a determining unit configured for determining information, which comprises a characterization of the circumferential edge of at least part of the singularized wafer for alignment purposes.

2. The apparatus according to claim 1, wherein the electromagnetic radiation source is arranged on and/or in the receptacle.

3. The apparatus according to claim 1, wherein the electromagnetic radiation source comprises at least one of the group consisting of a two-dimensional array of electromagnetic radiation elements, and an electromagnetic radiation emitting layer.

4. The apparatus according to claim 1, wherein the electromagnetic radiation source comprises at least one light-emitting diode.

5. The apparatus according to claim 1, wherein the detection unit is configured for detecting electromagnetic radiation passing through gaps between respectively adjacent singularized electronic chips of the wafer.

6. The apparatus according to claim 1, wherein the determining unit is further configured for determining further information relating to at least one of the group consisting of at least part of the singularized wafer and at least part of the electronic chips based on the detected electromagnetic radiation.

7. The apparatus according to claim 1, comprising a carrier for carrying the electronic chips and being transparent for the electromagnetic radiation.

8. The apparatus according to claim 7, wherein the electromagnetic radiation source is integrated in or is attached to the carrier.

9. The apparatus according to claim 1, comprising an expansion unit configured for spatially expanding a flexible carrier carrying the electronic chips to thereby increase a distance between adjacent electronic chips during inspection.

10. A method of inspecting a plurality of electronic chips singularized from a wafer, the method comprising:
    mounting the wafer on or over a receptacle, which is configured for both handling and inspection of the plurality of electronic chips;
    illuminating at least part of a first main surface of the singularized wafer with electromagnetic radiation;
    detecting electromagnetic radiation along at least part of a circumferential edge of the singularized wafer from a side facing a second main surface of the singularized wafer and opposing the first main surface; and
    determining information, which comprises a characterization of the circumferential edge of at least part of the singularized wafer for alignment purposes.

11. The method according to claim 10, wherein the method comprises determining further information relating to at least one of the group consisting of at least part of the singularized wafer and at least part of the electronic chips based on the detected electromagnetic radiation.

12. The method according to claim 11, wherein the determined further information comprises information indicative of a distance between adjacent electronic chips in at least one direction.

13. The method according to claim 11, wherein the determined further information comprises information indicative of a dimension of at least part of the electronic chips in at least one direction.

14. The method according to claim 11, wherein the determined further information comprises an identification of at least one missing singularization region in which adjacent electronic chips have not been singularized.

15. The method according to claim 11, wherein the determined further information comprises information indicative of a number of alignment markers on at least part of the electronic chips.

16. The method according to claim 11, wherein the determined further information comprises information indicative of a position of at least one of the electronic chips.

17. The method according to claim 11, wherein the determined further information comprises information indicative of a position of at least one alignment marker on at least part of the electronic chips.

18. The method according to claim 11, wherein the method comprises detecting electromagnetic radiation having passed from the first main surface through the singularized wafer to the second main surface.

* * * * *